Figure 1:
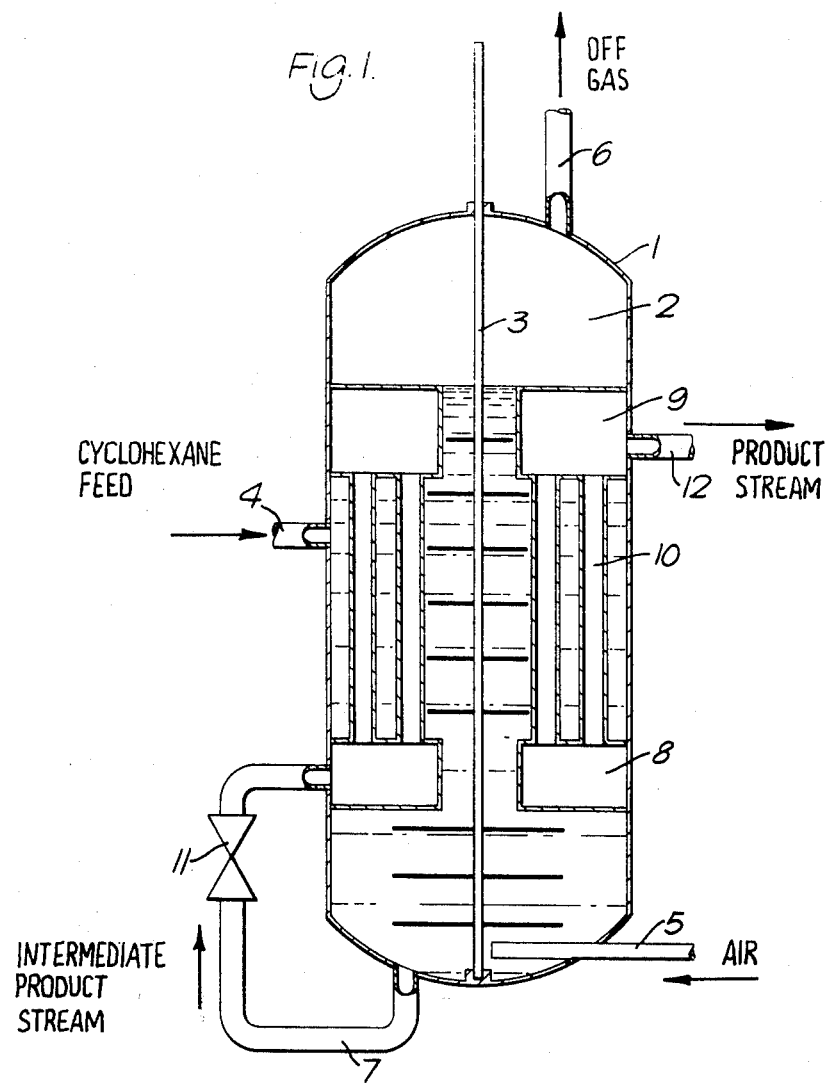

United States Patent [19]

Langley et al.

[11] 4,055,600

[45] Oct. 25, 1977

[54] CYCLOHEXANE OXIDATION PROCESS

[75] Inventors: Philip Edward Langley; Robert Tulip, both of Middlesbrough, England

[73] Assignee: Imperial Chemical Industries Limited, London, England

[21] Appl. No.: 629,554

[22] Filed: Nov. 6, 1975

[30] Foreign Application Priority Data

Nov. 21, 1974 United Kingdom ............... 50443/74

[51] Int. Cl.$^2$ ..................... C07C 27/12; C07C 29/00; C07C 45/02; C07C 179/02
[52] U.S. Cl. ........................... 260/586 P; 260/597 R; 260/610 B; 260/617 H; 260/631 R; 260/632 C
[58] Field of Search ............ 260/586 P, 631 R, 610 B, 260/632 C, 597 R, 617 H

[56] References Cited

U.S. PATENT DOCUMENTS

| 2,429,115 | 10/1947 | Atkins | 260/586 P |
|---|---|---|---|
| 2,557,281 | 6/1951 | Hamblet et al. | 260/631 R |
| 2,825,742 | 3/1958 | Schueler et al. | 260/586 P |
| 3,274,254 | 9/1966 | Seddon | 260/586 P |
| 3,551,482 | 12/1970 | Ger et al. | 260/586 P |
| 3,564,058 | 2/1971 | Bang et al. | 260/586 P |
| 3,932,513 | 1/1976 | Russell | 260/586 P |

Primary Examiner—Norman Morgenstern
Attorney, Agent, or Firm—Cushman, Darby & Cushman

[57] ABSTRACT

Aliphatic or cycloaliphatic hydrocarbons (especially cyclyhexane) are oxidized in the liquid phase with an oxygen-containing gas at low conversion in a reactor comprising two contacting compartments allowing heat transfer from one to the other, the first operating at a higher pressure than the second into which the reaction mixture from the first is released so effecting cooling, partial evaporation of the excess hydrocarbon and concentration of the oxidation product.

8 Claims, 2 Drawing Figures

CYCLOHEXANE OXIDATION PROCESS

This invention relates to an oxidation process, and more particularly to a proces for the oxidation of aliphatic or cycloaliphatic hydrocarbons with an oxygen-containing gas.

It is already known to oxidise aliphatic or cycloaliphatic hydrocarbons in the liquid phase with a gas containing molecular oxygen, especially air, to give the corresponding alcohols and/or ketones. A particularly important instance is the oxidation of cyclohexane to a mixture of cyclohexanol and cyclohexanone, the so-called 'KA'. In order to reduce the proportion of unwanted by-products in this reaction, it is customary to only partially oxidise the hydrocarbon, so that the conversion of hydrocarbon is usually below 20%, frequently below 10% and in some cases below 5%. A disadvantage of low conversions is that a large proportion of unoxidised hydrocarbon has to be recovered from the oxidation product, distillation being the only method normally used in commercial practice, and then recycled, and this requires large plant investment and a large energy input. At the same time the temperature of the oxidising reaction mixture requires careful control by some form of cooling.

We have now devised a process employing a special reactor whereby, although the oxidation is taken only to a low degree of conversion, a product with a higher concentration of oxidation product is obtained from the reactor, and whereby the concentration of the oxidation product and the cooling of the oxidising reaction mixture are achieved with interchange of heat between the two stages in the reactor. This results in a more economical utilisation of heat energy and in a reduction of the size of the equipment required for separating the oxidation product from the reactor effluent stream.

The invention provides a process for the oxidation of an aliphatic or cycloaliphatic hydrocarbon in the liquid phase with a gas containing molecular oxygen to an oxidation product, in which, in the oxidation stage, only a minor proportion of the hydrocarbon feed is oxidised, which process comprises continuously feeding the liquid hydrocarbon to the first compartment of a reactor comprising two compartments in physical contact with each other so as to allow heat transfer from one to the other, continuously introducing oxygen-containing gas into the liquid hydrocarbon in the first compartment to effect partial oxidation thereof to a liquid comprising hydrocarbon and oxidation product, continuously releasing the so oxidised liquid from the first compartment to the second compartment operating at a lower pressure wherein a part of the unoxidised liquid hydrocarbon therein is vaporised with extraction of heat from the oxidising mixture in the first compartment, and continuously removing from the second compartment a vapour comprising hydrocarbon and a liquid, comprising hydrocarbon and oxidation product, with a higher concentration of oxidation product than the liquid released from the first compartment.

The reactor used in the process of our invention contains two compartments in physical contact to allow heat transfer from one to the other. Any type of reactor which fulfils these conditions is suitable. Especially suitable, however, is a reactor in which one compartment comprises tubes or passages passing through the other compartment. In such a reactor the area of contact between the two compartments and hence the efficiency of heat transfer can be increased by increasing the number of tubes or passages. Alternatively, or in addition, the surface areas of the boundary walls between the two compartments may be increased by having them in corrugated or crenellated form. Moreover, any tube or passage may be finned to increase the rate of heat transfer. The second compartment operates at a lower pressure than the first, so that the passage of liquid from the first to the second is through a pressure reducing means such as a pressure reducing valve.

The reduction of pressure when the liquid is released from the first compartment into the second results in vaporisation of part of the unoxidised liquid hydrocarbon therein with consequent temperature reduction. The product stream is removed from the second compartment of the reactor either as a single stream consisting of vapour and liquid, in which case it is subsequently separated into vapour and liquid, or as separate vapour and liquid streams.

The oxidation in the first compartment may, if desired, be carried out in the presence of oxidation catalysts such as are already known for such oxidations. The catalyst may be, for example, a metal salt, e.g. a cobalt or manganese salt, especially a salt which is soluble in the hydrocarbon medium, for example salts of long chain fatty organic acids. As particular examples of such catalysts there may be mentioned cobalt stearate, cobalt octoate and cobalt naphthenate. In the presence of such a catalyst the oxidation product consists of the alkanol or cycloalkanol corresponding with the aliphatic or cycloaliphatic hydrocarbon which is oxidised, possibly together with the corresponding alkanone or cycloalkanone and the corresponding alkane hydroperoxide or cycloalkane hydroperoxide which is formed as an intermediate in the oxidation of the hydrocarbon to the alcohol, but which tends to decompose to the alcohol in the presence of metallic catalysts. Each of these forms a useful constituent on the total oxidation product.

Alternatively, however, the oxidation may be effected in the absence of catalyst and in this case, especially when the oxidation is effected at low conversion, for example at less than 5% conversion, the product is rich in the hydroperoxide, together, however, with the alcohol and the ketone. The hydroperoxide in the oxidation product obtained from the reactor may subsequently be converted to alcohol and ketone by methods known in themselves, for example by thermal decomposition, by catalytic decomposition or by reduction.

The temperature during the oxidation in the first compartment may vary over quite wide ranges, for example from 50° to 250° C, but is preferably within the range 100° to 200° C. The pressure in the first compartment is higher than in the second compartment. Though there is no upper limit of pressure, very high pressures offer no advantage and pressures in the first compartment will normally be in the range from 3 to 50 bar absolute. It is an advantage of our process that it is unnecessary to cool the oxidising reaction mixture by allowing the hydrocarbon to evaporate, since cooling is available through contact with the second compartment and in consequence pressures in the oxidation compartment may be higher than when evaporative cooling is necessary. In addition, since higher pressures within the oxidation compartment are possible because of indirect heat removal, the required vessel will be smaller than would otherwise be required, because of the reduced quantity of off gas. It will normally be advantageous to heat the hydrocarbon prior to its introduction into the first compartment.

The pressure in the second compartment is lower than in the first, the pressure drop being such as to cause vaporisation of part of the hydrocarbon in the liquid released from the first compartment. Normally it is advantageous for there to be at least a slight positive pressure in the second compartment above that of the atmosphere, but the use of lower pressures than that of the atmosphere are not excluded. Pressures in the second compartment will normally be in the range from 0.5 to 10 bar absolute. The temperature of the liquid in the second compartment is lower than that in the first, the difference in temperature normally being in the range 10° to 100° C.

The gas containing molecular oxygen used in the oxidation may be molecular oxygen itself but is conveniently air or other mixtures of nitrogen and oxygen with a higher or lower proportion of oxygen than that of air, obtained, for example, by mixing oxygen or nitrogen with air. It may also be advantageous for the oxidant gas to contain a proportion of ozone. It will normally be arranged for the gas effluent from the oxidation compartment to have an oxygen content not greater than about 8% by volume to avoid explosion hazards, and this may be controlled by varying the air rate and other reaction parameters.

The degree of conversion at the oxidation stage in the first compartment will normally be below 20% and preferably below 10%. Where it is chosen to oxidise primarily to the hydroperoxide in the absence of a catalyst the conversion will preferably be below 5%. The increase in the concentration of the oxidation product in the oxidised liquid in the second compartment will preferably be such that the concentration of the oxidation product in the liquid effluent from the second compartment is from 5 to 50%.

The residence time of the hydrocarbon in the oxidation compartment may vary widely depending on the conditions employed and the degree of conversion required. The residence time may vary from a few minutes to several hours, for example from 3 minutes to 5 hours. At low conversions (below 5%) quite short residence times are possible, e.g. from 3 to 15 minutes, thus allowing the size of the plant and the quantity of material in the plant to be limited.

The process of our invention is particularly valuable for the oxidation of cycloaliphatic hydrocarbons or naphthenes. Particularly suitable starting materials are cyclopentane, cyclohexane, cycloheptane, cyclooctane, cyclodecane and cyclododecane, and their mono- or poly-alkyl substituted derivatives thereof, for example methylcyclopentane and methylcyclohexanes. The process is of special importance for the oxidation of cyclohexane, especially for its oxidation at low conversion in the absence of catalyst to give primarily cyclohexyl hydroperoxide for subsequent conversion by known methods, especially by catalytic hydrogenation, into cyclohexanol and cyclohexanone.

When oxidising cyclohexane in the absence of catalyst it is preferred that the temperature of the oxidising liquid in the first compartment is in the range 150° to 200° C, more preferably 160° to 190° C. The pressure in that compartment is preferably from 8 to 50 bar absolute, more preferably 11 to 40 bar absolute. The degree of conversion in the first compartment is preferably from 2 to 4% and the residence time from 5 to 10 minutes. After concentration in the second compartment the concentration of the oxidation product (mainly cyclohexyl hydroperoxide) in the liquid effluent from the second compartment is preferably from 5 to 15%. The pressure in the second compartment is preferably in the range 2 to 5 bar absolute and the temperature preferably in the range 115° to 140° C.

Figure 2:
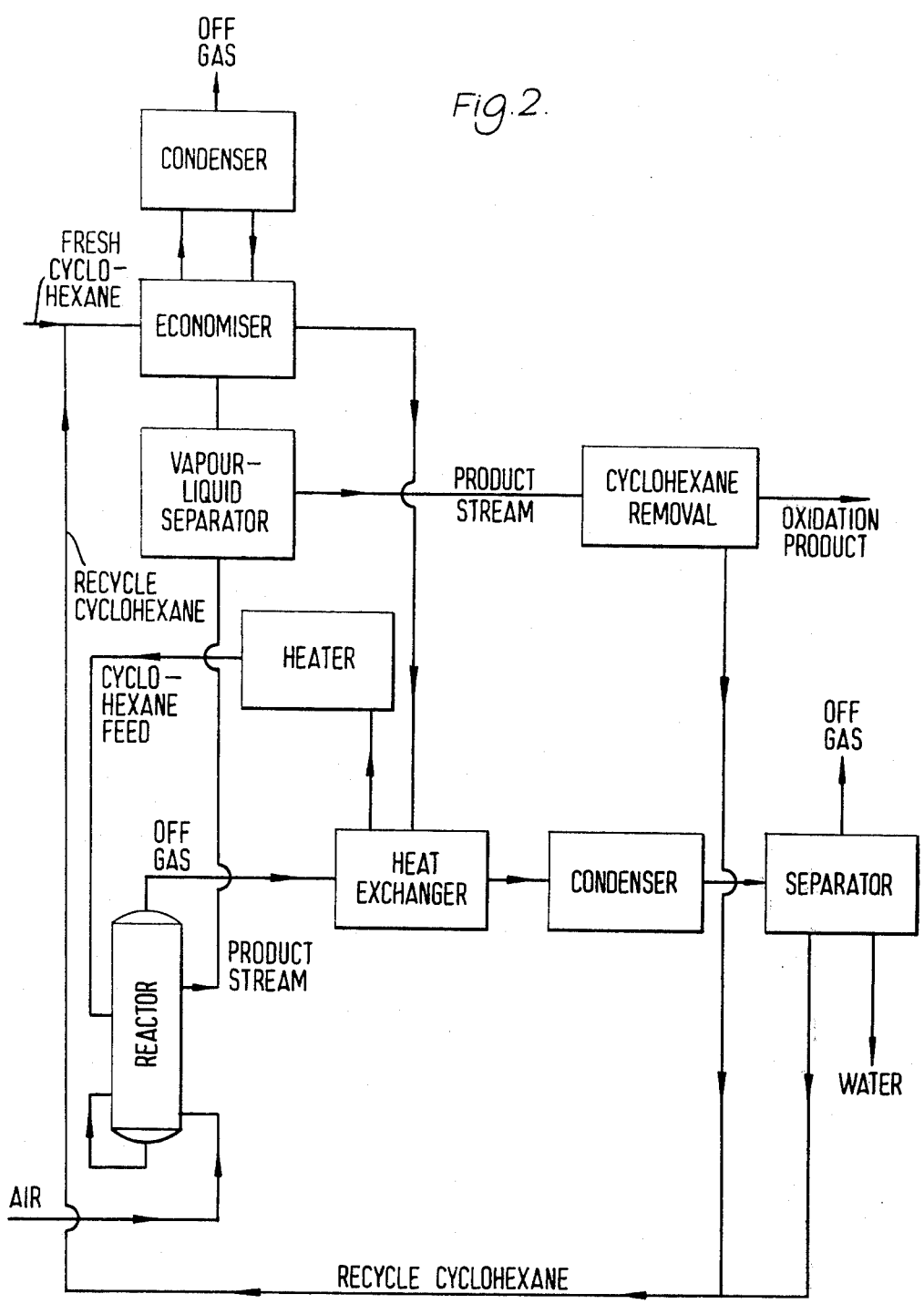

Our invention will be more clearly understood by reference to the drawings in which FIG. 1 is an elevation in axial section of a reactor for use in the process of our invention and FIG. 2 is a flow sheet showing how materials entering and leaving the reactor are handled. In FIG. 1, 1 is a vertical cylindrical reactor with dished ends, 2 is the compartment for the oxidation fitted with a vertical agitator 3, inlets for hydrocarbon 4 and for air 5, and exits for off-gases 6 and for liquid 7. Fixed within compartment 2 is a separate second compartment of an annular configuration comprising a base portion 8 and a header portion 9, connected to each other by a series of vertical tubes 10 passing through the compartment 2. The exit 7 for liquid from compartment 2 is connected via a pressure reducing valve 11 to the base portion 8 of the second compartment, and the header portion 9 is fitted with an exit 12 for liquid and vapour. In operation, with the agitator 3 working, heated cyclohexane is continuously introduced via the inlet 4, the liquid level in compartment 2 being maintained in the region of the header portion 9 of the second compartment, and air is introduced via inlet 5 to effect oxidation, the off-gases leaving via exit 6. the oxidised liquid is released via exit 7 and pressure reducing valve 11 to the base portion 8 of the second compartment. Under the lower pressure in the second compartment some cyclohexane is vaporised thereby extracting heat from the oxidation compartment and cyclohexane vapour and the residual oxidised liquid leave via the exit 12. Typical operating parameters are a temperature of 175° C and a pressure of 30 bar absolute in the oxidation compartment 2, and a temperature of 117° C= and a pressure of 2.7 bar absolute, in the second compartment. The conversion in the oxidation compartment is typically 3.5% with a residence time of 6 to 7 minutes. The liquid separated from the product stream typically contains 10% of oxidation product.

A suitable method of handling the inlet and exit streams to and from the reactor is illustrated in the flow sheet of FIG. 2, although other methods are possible and our invention is not limited thereby. The off-gases leaving the reactor via exit 6 contain residual air of reduced oxygen content, cyclohexane vapour and water vapour formed during the oxidation. The hot off-gases pass through a heat exchanger to heat the incoming cyclohexane and then pass to a condenser to condense out water and cyclohexane, which are separated, and the recovered liquid cyclohexane recycled to the reactor. The residual off-gases are passed to a cyclohexane absorption section before being released to the atmosphere. The mixed liquid and vapour product stream leaving the reactor via exit 12 passes to a vapour-liquid separator. The cyclohexane vapour from the separator passes to an economiser where it meets the incoming cyclohexane feed in counter-current flow and gives up part of its heat thereto, any residual cyclohexane vapour being condensed in a condenser and returned to the economiser. The liquid stream from the separator is passed to the cyclohexane removal section where part of the cyclohexane is removed by distillation and recycled to the reactor, and the oxidation product, comprising typically cyclohexylhydroperoxide 7.9%, cyclohexanol 5.6%, cyclohexanone 5.9%, other oxidation products 2.4% and cyclohexane 78.2% is removed. It may be treated to convert the cyclohexylhydroperoxide to cyclohexanol, for example by catalytic hydrogenation, and the mixed cyclohexanol and cyclohexanone separated from the cyclohexane by distillation. The liquid cyclohexane feed after being heated by passing through the economiser and the heat exchanger heated by the off-gases, is finally passed through a heater to bring it to the desired inlet temperature.

The oxidation product of our invention is valuable for use in making intermediates for polymers. Thus cyclohexanol, obtained from cyclohexyl hydroperoxide by known methods, and its mixtures with cyclohexanone may be oxidised, for example with nitric acid in the presence of a metallic catalyst, to give adipic acid, useful in the manufacture of polyesters and polyamides, especially the nylons by polycondensation with diamines, for example by polycondensation with hexamethylene diamine to give nylon 6,6. Alternatively, cyclohexanone, obtainable from cyclohexanol by dehydrogenation, may be converted to the oxime, and thence by the Beckmann re-arrangement to caprolactam, the monomer for nylon 6.

We claim:

1. In a process for the oxidation of cyclohexane wherein the liquid cyclohexane and a gas containing molecular oxygen are continuously fed to a reactor operating at elevated temperature under pressure and wherein the liquid cyclohexane in absence of catalyst is converted to the extent of less than 5% to an oxidation product consisting essentially of cyclohexylhydroperoxide, cyclohexanol and cyclohexanone, and a liquid mixture of cyclohexane and the said oxidation product is continuously removed from the reactor, the improvement consisting essentially of conducting the oxidation in a two compartment reactor, the two compartments contacting each other to allow heat transfer between them, and releasing the entire reaction mixture in the first compartment in which the degree of conversion of cyclohexane is from 2 to 4% directly from the first compartment at a pressure in the range 8 to 50 bar absolute and a temperature in the range 150° to 200° C to the second compartment operating at a lower pressure in the range 2 to 5 bar absolute and a lower temperature in the range 115° to 140° C, whereby part of the cyclohexane is vaporized, and a liquid mixture of cyclohexane and oxidation product containing from 5 to 15% of oxidation product is continuously removed from the reactor.

2. The process of claim 1 in which the reactor is one in which one compartment comprises tubes or passages passing through the other compartment.

3. The process of claim 1 in which the temperature during oxidation in the first compartment is from 50° to 250° C.

4. The process of claim 1 in which the pressure in the first compartment is from 3 to 50 bar absolute.

5. The process of claim 1 in which the pressure in the second compartment is from 0.5 to 10 bar absolute.

6. The process of claim 1 in which the temperature of liquid in the second compartment is lower than that in the first by from 10° to 100° C.

7. The process of claim 1 in which the degree of conversion of the cyclohexane at the oxidation stage in the first compartment is below 20%.

8. The proces of claim 1 in which the concentration of the oxidation product in the liquid effluent from the second compartment is from 5 to 50% by weight.

* * * * *